United States Patent
Hamilton et al.

[11] Patent Number: 6,129,737
[45] Date of Patent: *Oct. 10, 2000

[54] ASYMMETRIC DILATATION BALLOON

[75] Inventors: Bruce S. Hamilton, Lowell; David B. Vafiades, Bedford; Ralph J. Barry, Hudson; Arthur R. Mandenjian, Winchester; Daniel J. Kalashian, Watertown, all of Mass.

[73] Assignee: Boston Scientific Corporation, Watertown, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/726,548

[22] Filed: Oct. 7, 1996

Related U.S. Application Data

[63] Continuation of application No. 08/204,644, Mar. 1, 1994, abandoned.

[51] Int. Cl.[7] .................................................. A61M 29/00
[52] U.S. Cl. .............................. 606/194; 604/96; 604/916
[58] Field of Search ............................... 604/96–99, 101, 604/104, 916; 606/191, 192, 194, 198

[56] References Cited

U.S. PATENT DOCUMENTS

| | | | |
|---|---|---|---|
| 2,308,484 | 1/1943 | Auzin et al. ................................. | 18/58 |
| 3,889,685 | 6/1975 | Miller, Jr. et al. ....................... | 128/348 |
| 3,971,385 | 7/1976 | Corbett .................................... | 128/351 |
| 4,018,230 | 4/1977 | Ochiai et al. ............................ | 128/344 |
| 4,364,394 | 12/1982 | Wilkinson .................................. | 604/96 |
| 4,413,989 | 11/1983 | Schjeldahl et al. ........................ | 604/96 |
| 4,630,609 | 12/1986 | Chin ......................................... | 128/344 |
| 4,689,041 | 8/1987 | Corday et al. ............................. | 604/53 |
| 4,726,373 | 2/1988 | Greengrass ................................ | 128/343 |
| 4,777,951 | 10/1988 | Cribier et al. ........................... | 128/344 |
| 4,793,359 | 12/1988 | Sharrow .................................... | 128/658 |
| 4,834,093 | 5/1989 | Littleford et al. ................... | 128/303.1 |
| 4,850,348 | 7/1989 | Pell et al. ............................ | 128/207.15 |
| 4,927,412 | 5/1990 | Menasche ................................... | 604/96 |
| 4,932,956 | 6/1990 | Reddy et al. ............................ | 606/192 |
| 4,941,877 | 7/1990 | Montano, Jr. .............................. | 604/96 |
| 4,943,278 | 7/1990 | Euteneuer et al. ........................ | 604/96 |
| 4,964,853 | 10/1990 | Sugiyama et al. ......................... | 604/96 |
| 4,994,032 | 2/1991 | Sugiyama et al. ......................... | 604/96 |
| 5,020,534 | 6/1991 | Pell et al. ............................ | 128/207.15 |
| 5,021,045 | 6/1991 | Buckberg et al. ......................... | 604/53 |
| 5,030,227 | 7/1991 | Rosenbluth et al. ..................... | 606/192 |
| 5,042,985 | 8/1991 | Elliott et al. ............................ | 606/192 |
| 5,078,725 | 1/1992 | Enderle et al. .......................... | 606/193 |
| 5,108,414 | 4/1992 | Enderle et al. .......................... | 606/193 |
| 5,146,925 | 9/1992 | Snow ....................................... | 128/658 |
| 5,147,385 | 9/1992 | Beck et al. ................................. | 623/1 |
| 5,163,989 | 11/1992 | Campbell et al. ......................... | 65/110 |
| 5,195,969 | 3/1993 | Wang et al. ............................... | 604/96 |
| 5,273,536 | 12/1993 | Savas ....................................... | 604/96 |
| 5,312,430 | 5/1994 | Rosenbluth et al. ..................... | 606/192 |
| 5,338,298 | 8/1994 | McIntyre . | |

FOREIGN PATENT DOCUMENTS

WO 91/09640 7/1991 WIPO .

*Primary Examiner*—Corrine McDermott
*Attorney, Agent, or Firm*—Fish & Richardson P.C.

[57] ABSTRACT

Dilating an obstructed region in a narrow, highly torturous lumen with a dilatation catheter having near its distal end an inflatable balloon with a dilatation section, a proximal taper section, and distal taper section. The dilatation section is generally cylindrical in shape when the balloon is inflated. The distal taper section has a relatively abrupt slope, and the proximal taper section has a relatively gradual slope.

21 Claims, 3 Drawing Sheets

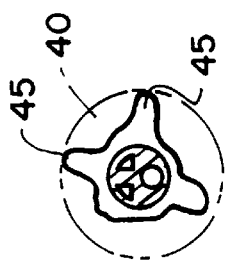
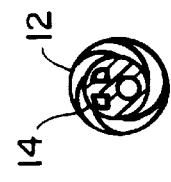
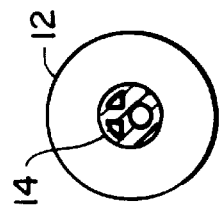
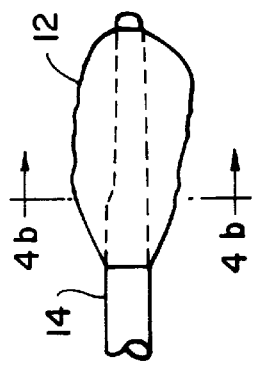
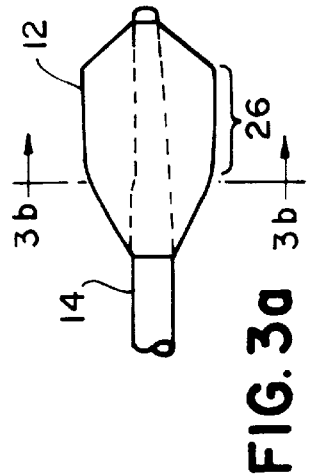
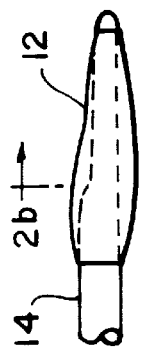
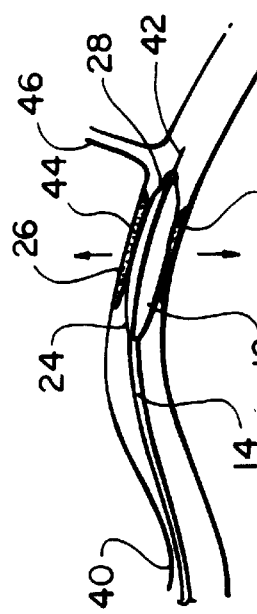
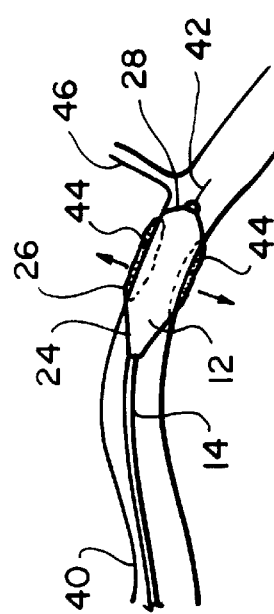
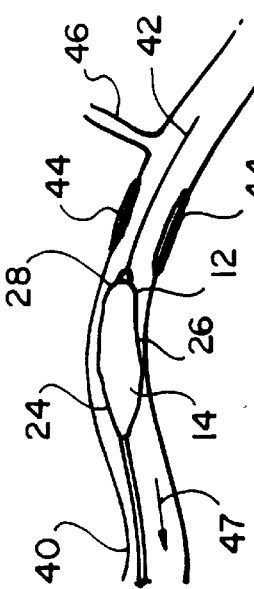

ASYMMETRIC DILATATION BALLOON

This is a continuation of application Ser. No. 08/204,644, filed Mar. 1, 1994, now abandoned.

FIELD OF THE INVENTION

This invention relates to dilatation catheters and balloons.

BACKGROUND OF THE INVENTION

Dilatation balloons are carried on the end of long catheters that can be threaded through a body lumen. The balloon is positioned adjacent an occluded site in the lumen and inflated to dilate the site using force applied by pressure in the balloon. The balloon is then deflated and the catheter is removed from the body.

SUMMARY OF THE INVENTION

In a first aspect, the invention features a method for dilating an obstructed region in a narrow, highly torturous lumen where the obstructed region is proximally adjacent to a physiological feature such as a lumenal side branch, an extreme curvature, or a lumen termination. The method includes providing a dilatation catheter having near its distal end an inflatable balloon with a dilatation section, a proximal taper section, and distal taper section. The dilatation section is generally cylindrical in shape when the balloon is inflated. The distal taper section has a relatively abrupt slope, and the proximal taper section has a relatively gradual slope. The method also includes placing the catheter into the lumen with the balloon in the deflated state and wrapped about the catheter to present a small diameter profile, positioning the balloon so that the dilatation section is adjacent the obstructed region and the distal taper section is adjacent the physiological feature, the abrupt slope allowing the positioning without the catheter interfering with the feature, inflating the balloon to engage the dilatation section with the obstructed region and to dilate the region by force applied by the dilatation section. The method also includes deflating the balloon, and withdrawing the catheter from the lumen, the gradual profile of the proximal taper facilitating atraumatic removal of the catheter from the body.

In another aspect, the invention features a dilatation catheter having a catheter body constructed for delivery through a torturous lumen in the body to an occluded site and having near its distal end a balloon being inflatable and deflatable by passing fluid through the catheter. The balloon includes a relatively long dilatation section extending substantially parallel to the axis of the catheter when the balloon is in the inflated state for engaging the wall of the lumen and dilating the occluded site, a proximal taper section having a relatively gradual slope providing a gradual, atraumatic profile upon withdrawal of the catheter from the body after dilatation, and a distal taper region having a relatively abrupt slope.

Embodiments may include one or more of the following features. The proximal taper section has a taper angle of about 3–15° and the distal taper section has a taper angle of about 10–35°. The proximal taper has a taper angle of about 10° and the distal taper section has a taper angle of about 20°. The distal and proximal taper sections have differing taper angles selected to maintain a balloon volume equal to or less than a balloon having equal proximal and distal tapers of an equal taper angle between 8–12°, e.g. 10°. The balloon includes a relatively inelastic polymer. The balloon includes PET.

The invention provides a balloon catheter with an important combination of features. Since the balloons of the invention have a relatively gradual proximal taper, they can be withdrawn from a torturous lumen with less trauma even if the balloon deflates into an irregular lumen-wall engaging configuration. Since the balloons of the invention have a short, abrupt distal taper, they provide the advantage that the balloon and catheter can be located such that the dilatation surface is adjacent an occluded region without the distal portions of the device interfering with a physiological feature, such as a lumenal side branch. Since the taper angle of the proximal and distal tapered regions are coordinated, balloon volume can be controlled to affect rapid inflate/deflate times. The invention provides these advantages over symmetric balloons that have abrupt taper angles since those balloons are less likely to refold into an atraumatic configuration after deflation. The invention provides advantages over symmetric balloons with gradual tapers since those balloons have relatively large volumes and do not allow operation in areas with interfering physiological features.

BRIEF DESCRIPTION OF THE DRAWING

FIG. 2 is a side view of a catheter according to the invention being delivered into a torturous lumen, while FIG. 2a is an enlarged side view of the distal end of the catheter having the balloon thereon, and FIG. 2b is a cross-sectional view of the distal end of the catheter having the balloon thereon;

FIG. 3 is a side view of a catheter according to the invention undergoing inflation at the stenosed site, while FIG. 3a is a side view of the distal end of the catheter having the balloon thereon and FIG. 3b is a cross-sectional view of the end of the catheter having the balloon thereon;

FIG. 4 is a side view of a catheter according to the invention after the balloon has been deflated following dilatation; while FIG. 4a is an enlarged side view of the catheter having the balloon thereon, and FIG. 4b is a cross-sectional view of the end of the catheter having the balloon thereon;

FIG. 6 is a cross-sectional view of a multilayer balloon.

DESCRIPTION OF THE PREFERRED EMBODIMENTS

Figure 1:
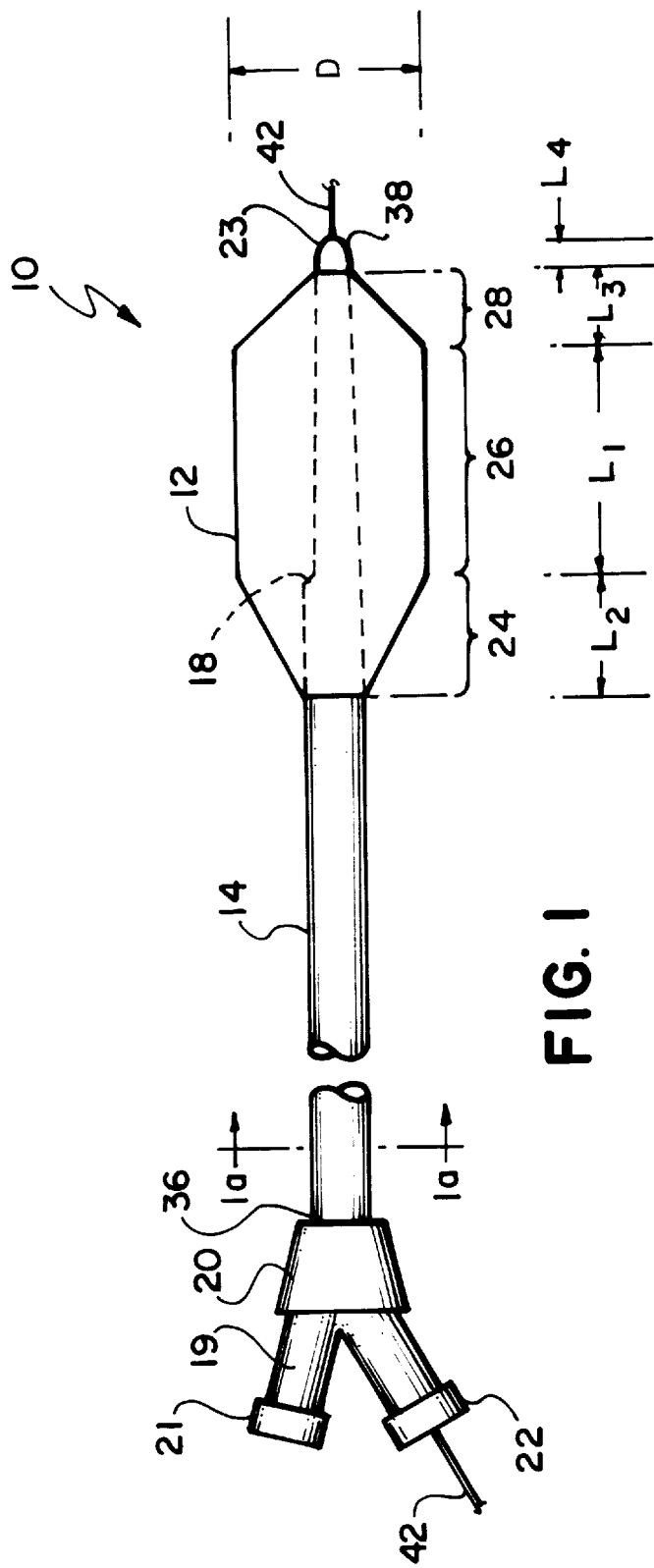
FIG. 1 is a side view of a dilatation catheter according to the invention.
Figure 1A:
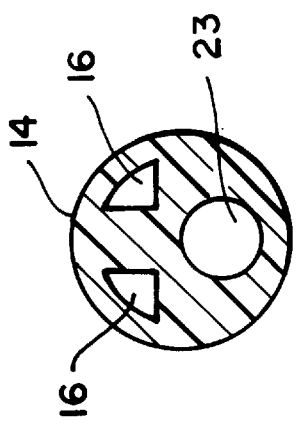
FIG. 1a is a cross-sectional view along the lines a—a in FIG. 1.

Referring to FIGS. 1 and 1a, a dilatation catheter 10 according to the invention includes an asymmetric balloon 12 attached to a catheter 14. Asymmetric balloon 12 has a gently tapered proximal portion 24, a uniform, cylindrical working or dilatation surface 26, and a sharply tapered, abrupt distal portion 28. As will be discussed in more detail below, the long taper on proximal portion 24 permits atraumatic withdrawal of dilatation catheter 10 when the balloon is deflated, while the short taper on the distal portion 28 permits inflation of asymmetric balloon 12 for dilatation of a stenosis in an area where there is little distal clearance beyond a stenosis or lesion because of a physiological feature. The short taper on the distal portion 28 also results in reduced volume relative to a comparably sized balloon having a long taper on both ends, which, in turn, results in decreased inflation/deflation times.

Referring particularly to FIGS. 2 and 2a, in use, the catheter 12 is threaded through a highly torturous lumen 40, such as the femoral, renal or coronary artery where there are many side branches, such as side branch 46. The lumen 40 includes a stenosed region 44 which is located just proximal of the side branch 46. As illustrated, the catheter is delivered over a guidewire 42 such that the working surface 26 of the balloon is adjacent the stenosed region 44 and the distal taper 28 along with portions of the catheter distal thereof do not occlude or interfere with the side branch 46.

Referring particularly to FIGS. 2a and 2b, for delivery and positioning of the catheter, the balloon 12 is folded about the catheter body using a technique known in the art as "wing folding" to provide a smooth, low radial profile that prevents the catheter from being hung up on sharp turns in the lumen and thereby causing trauma by abraiding the lumen walls.

Referring to FIG. 3, once properly positioned, the balloon is then inflated such that the working surface 26 engages the stenosed region 44 and presses it outward, dilating the region by pressure. During the inflation, the distal portion 28, with the short taper expands radially somewhat but still does not interfere with the side branch 46. Referring particularly to FIGS. 3a and 3b, the working surface 26 forms a substantially cylindrical outer profile when the balloon is fully inflated.

Referring to FIG. 4, after the region has been dilated, the balloon is deflated. Referring particularly to FIGS. 4a and 4b, in some instances upon deflation, the balloon may not return to a smooth, low profile configuration. Rather, the balloon may take on an irregular configuration including radial extensions 45. This may be caused by, for example, the influence of an irregular body lumen wall which can engage the balloon as a vacuum draws inflation fluid from it. As a balloon in this condition is withdrawn proximally through the torturous lumen (arrow 47), these extensions can engage the walls of the lumen 40. The proximal portion 24 of the balloon, including the gentle taper, presents a relatively gradual sloping surface to the lumen wall, which allows the catheter to be removed with less trauma. Moreover, the gradual taper encourages the balloon to gradually and gently refold as the taper engages the tissue wall, as opposed to causing the material to build up and jam the catheter in the body lumen. The force required to withdraw the catheter is generally reduced. In addition, the balloon may provide a smaller folded profile than a balloon with a symmetric, abrupt taper, allowing delivering into the body through smaller introducer catheters. The balloon may also be more easily withdrawn into the introducer catheter after deflation.

Other important applications for the invention include highly torturous lumens including an occlusion at a location adjacent a sharp turn or an occlusion adjacent a lumenal end-wall. In all of these cases, treatment will be facilitated by the combination of a relatively gradual proximal taper that allows the catheter to be removed from the torturous lumen after the balloon has been deflated and a short abrupt distal taper that does not interfere with the distal physiological feature.

Asymmetric balloon 12 is preferably made of a nondistendable material. Nondistendable balloons are typically include polymers, such as polyethylene terephthelate. (PET), which are relatively stiff and non-compliant and therefore may tend to form irregular configurations upon deflation which can abraid the wall of a body lumen. In embodiments, the balloon is formed substantially of PET. In other embodiments, the balloon may be a multi-layer balloon including an inner layer of PET and an outer layer of an engineering film plastic elastomer. Multi-layer balloons are discussed in Wang et al. U.S. Pat. No. 5,195,969 and U.S. Ser. No. 08/130,283 filed Oct. 1, 1993 the entire contents of both of which is hereby incorporated by reference. A cross sectional side-view of a balloon with multi-layers 8A, 8B is shown in FIG. 6. In other embodiments, the balloon may be formed of a blend of PET and other polymer materials (e.g. polyethylene) as discussed in U.S. Ser. No. 07/612,073, filed Nov. 9, 1990, the entire contents of which is incorporated herein by reference. Preferred wall thicknesses are between 0.3 to 3 thousandths of an inch, with the wall thickness of proximal section 24 being slightly greater than the wall thickness of distal section 28 to promote withdrawal in the event of a catastrophic failure to asymmetric balloon 12. The asymmetric taper arrangement according to the invention can also be used with balloons made of compliant polymers (e.g. polyethylene), especially in cases where these balloons are formed with relatively large wall thicknesses, which may have a greater resistance to deformation when the balloon engages a body lumen wall. Thus, the asymmetric balloon including the long proximal taper can also facilitate removal in compliant balloons.

Figure 5:
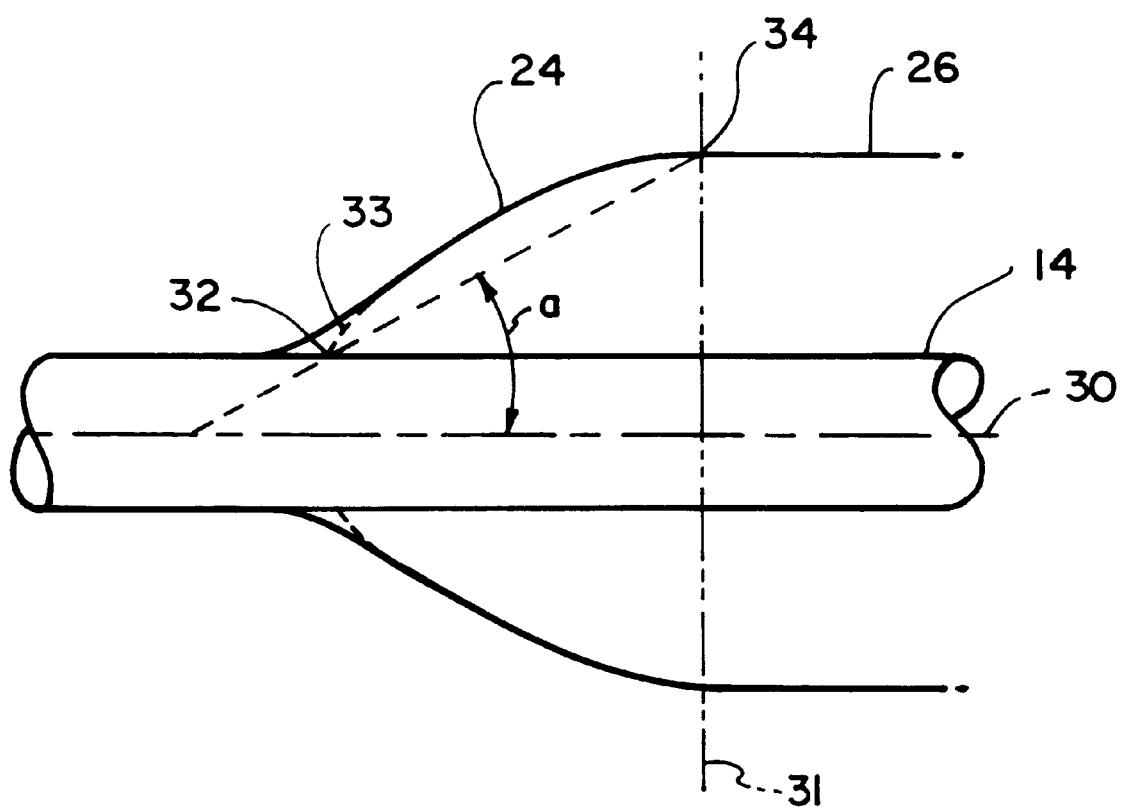
FIG. 5 is a partial cross-sectional side view of a catheter according to the invention illustrating measurement of taper angle.

Referring also to FIG. 5, transition taper angle "a" is the angle between longitudinal axis 30 and the line formed between point 34, at which the arc of the transition region of the balloon meets the cylindrical working surface 26, and the point 32, at which the arc of the transition region of the balloon meets the catheter 14. The radius arc of the transition region is illustrated at line 31. (As illustrated, the arc extends along the dotted line 33 to point 32 on catheter body 30, while the balloon itself extends to the catheter body at a region proximal of the point 32. The distal taper is measured in a similar manner.)

When asymmetric balloon 12 is inflated, proximal portion 24 forms a proximal taper angle "a" of between about 3 and 15°, preferably about 10°. Distal portion 28 forms a distal taper angle that is between 10 and 35°, preferably about 20°. Preferably, the taper angles of the proximal and distal sections are selected so that the balloon volume is equal to or less than a balloon having proximal and distal tapers of equal taper angles between 8–12°, preferably 10°. Preferably, the axial length of the working portion is greater than the axial extension of the distal or proximal portions. The inflation diameter of the working portion $d_1$, ranges from about 1.5 mm–20 mm, the length of the working portion $L_1$, ranges from 1 cm to 10 cm, the axial length of the proximal taper $L_2$ ranges from about 0.7 to 2 inches, and the axial length of the distal taper region ranges from about 0.40 to 1 inch. Typically, the dilatation section has a substantial length. In embodiments the balloons are constructed so that the length of the dilatation section is equal to or greater than the length of the proximal taper, e.g. the length of the dilatation section is twice the length or greater than the proximal taper. In embodiments, the dilatation section has a length that is twice the length or greater than the distal taper. In embodiments, the dilatation section has a length that is equal to or greater than the sum of the lengths of the two taper regions.

Referring back to FIGS. 1 and 1a, in a preferred embodiment, the proximal taper angle is 10°; the distal taper angle is 20°, and the working portion 26 has an inflated diameter, $d_1$, of about 8 mm, and an axial length of $L_1$, about 4 cm. In the deflated wing-folded state, the diameter of the catheter plus the balloon is about 0.081 inch. The proximal portion 24 extends an axial length $L_2$, about 0.68 inch. The distal portion 28 extends an axial length, $L_3$, about 0.36 inch. The distal portion terminates a distance $L_4$, about 6 mm, from the end of the catheter. The radius of the arc of the proximal transition portion is about 2.0147 inches and the radius of the arc of the distal transition section is about 0.4489 inches. This balloon has an inflation volume that is 15% less than a comparable balloon with both the distal section taper angle and the proximal section taper angle equal to 10°. For an asymmetric balloon constructed, as above but with balloon 2 cm dilatation section length, the asymmetric balloon has an inflation volume 21% less than a balloon with a distal section taper angle and proximal section taper angle equal to 10°. Balloon volume is an important consideration particularly for balloons that are to be used in the coronary arteries where inflation times must be typically kept to about 20 seconds or less. In most angioplasty operations, inflation time is important and typically kept to less than 1 minute.

Referring back now to FIGS. 1 and 1a, the asymmetric balloon 12 is inflated and deflated through a pair of inflation/deflation lumens 16 in the catheter body via an inflation/deflation port 18 located within the balloon. A bifurcation 19 is connected to the proximal end of the catheter 14 via strain relief element 20. Bifurcation 19 includes a first luer lock fitting 21 for connecting lumen 16 to a source of inflation fluid (not shown). Bifurcation 19 includes a second luer lock fitting 22 that allows insertion/removal of a guidewire 42 through a guidewire lumen 23 that runs through the entire length of the catheter 14. Typically for a balloon with an 8 mm inflated diameter, catheter 14 is made from nylon and is between 75 and 150 cm in length. Catheter 14 has a short (3 cm) taper from 75 thousandths (OD) of an inch to 68 thousandths of an inch at a location 40 cm from the distal tip. Guidewire lumen 23 is sized to accommodate a guidewire having a diameter of about 35 thousandths of an inch. A catheter that can be used with the balloons as taught herein are sold as the Ultrathin® balloon catheter by Boston Scientific Corporation, Watertown, Mass.

Other aspects are in the following claims. For example, the asymmetric balloon may be used in other vascular areas; and in non-vascular applications to similar effect and advantage.

What is claimed is:

1. A method of angioplasty in which a stenosis in a blood vessel is dilated, comprising:

providing a guidewire, and a dilatation catheter that is constructed for positioning in said blood vessel by sliding said catheter over said guidewire, said catheter having a flexible catheter body defining an axis and having a proximal end and a distal end, and near the distal end, said catheter body carrying an angioplasty balloon formed of a nondistendable polymer, said catheter body having a length of about 75–150 cm and defining a first lumen and a second lumen, said first lumen extending through said balloon and sized to slideably receive said guidewire, and said second lumen extending from the proximal end and including a port open to the interior of the balloon for introducing inflation fluid to inflate said balloon, the balloon including a dilatation section, a proximal taper section, and a distal taper section, said dilatation section extending substantially parallel to the axis of the catheter when the balloon is in the inflated state end over a sufficient length for engaging and dilating the stenosis by forcing the stenosis open under dilatation pressure, said proximal taper section having a gradual proximal slope to the catheter for providing a gradual, atraumatic profile upon withdrawal of said catheter from the blood vessel after dilatation, and said distal taper section having an abrupt distal slope extending a short length compared to said proximal taper section, placing said catheter into said blood vessel with said balloon in the deflated state and wrapped about said catheter to present a small diameter profile, positioning said catheter by sliding said catheter over a guidewire so that said dilatation section of said balloon is adjacent said stenosis, inflating said balloon while the balloon is within the stenosis to engage said dilatation section with said stenosis and to dilate said senosis by radial force applied by said dilatation section, deflating said balloon, and withdrawing said catheter body.

2. The method of claim 1 wherein said proximal taper section has a transition taper angle of about 3–15° and said distal taper section has a transition taper angle of about 10–35°.

3. The method of claim 2 wherein said proximal taper section has a transition taper angle of about 10° and said distal taper section has a transition taper angle of about 20°.

4. The method of claim 2 wherein said distal and proximal taper sections have differing transition taper angles selected to maintain a balloon volume that is in the range equal to or less than the volume of a balloon having the same dilatation section length and inflation diameter and proximal and distal taper sections of a matching transition taper angle between 8–12°.

5. The method of claim 1 wherein said balloon is composed of polymer including polyethyleneterephthalate.

6. The method of claim 1 wherein the proximal taper section has a transition taper angle of about 3 to 15°.

7. The method of claim 1 wherein the axial length of the dilatation section is greater than the axial length of the distal taper section or the proximal taper section.

8. The method of claim 1 wherein the axial length of the dilatation section is equal to or greater than the length of the proximal taper section.

9. The method of claim 1 wherein the axial length of the dilatation section is twice the length of the proximal taper section or greater.

10. The method of claim 1 wherein the axial length of the dilatation section is greater than the combined length of the proximal and distal taper sections.

11. A vascular dilatation catheter that is constructed for positioning in a blood vessel by sliding said catheter over a guidewire in an angioplasty operation in which a stenosis is dilated, comprising:

a flexible catheter body defining a device axis and having a proximal end and a distal end and, near the distal end, said catheter body carrying an angioplasty balloon formed of nondistendable polymer, said catheter body having a length of about 75–150 cm and defining a first and second lumen, said first lumen sized to slideably receive a guidewire for delivery of said catheter over a guidewire through said vessel to the stenosis, and said second lumen extending from the proximal end and including a port open to the interior of the balloon for introducing inflation fluid from the proximal end of said catheter to inflate said balloon, the balloon including a dilatation section, a proximal taper section, and a distal taier section, said dilatation section extending substantially parallel to the axis of the catheter when the balloon is in the inflated state and over a sufficient length for engaging and dilating the stenosis by forcing the stenosis open under dilatation pressure, wherein the length of the dilatation section is greater than the length of the distal taper section or the proximal taper section, said proximal taper section having a gradual proximal slone to the catheter for providing a aradual, atraumatic profile upon withdrawal of said catheter from the blood vessel after dilatation, and said distal taper section having an abruis distal slope extending a short length compared to said proximal taper section.

12. A vascular dilatation catheter that is constructed for positioning in a blood vessel by sliding said catheter over a guidewire in an angioplasty operation in which a stenosis is dilated, comprising:

a flexible catheter body defining a device axis and having a proximal end and a distal end and, near the distal end, said catheter body carrying an angioplasty balloon formed of nondistendable polymer, said catheter body having a length of about 75–150 cm and defining a first and second lumen, said first lumen sized to slideably receive a guidewire for delivery of said catheter over a guidewire through said vessel to the stenosis, and said second lumen extending from the proximal end and including a port open to the interior of the balloon for introducing inflation fluid from the proximal end of said catheter to inflate said balloon, the balloon including a dilatation section, a proximal taper section, and a distal taper section, said dilatation section extending substantially parallel to the axis of the catheter when the balloon is in the inflated state and over a sufficient length for engaging and dilating the stenosis by forcing the stenosis open under dilatation pressure, wherein the length of the dilatation section is equal to or greater than the length of the proximal taper section, said proximal taper section having a gradual proximal slope to the catheter for providing a gradual, atraumatic profile upon withdrawal of said catheter from the blood vessel after dilatation, and said distal taper section having an abrupt distal slope extending a short length compared to said proximal taper section.

13. A vascular dilatation catheter that is constructed for positioning in a blood vessel by sliding said catheter over a guidewire in an angioplasty operation in which a stenosis is dilated, comprising:

a flexible catheter body defining a device axis and having a proximal end and a distal end and, near the distal end, said catheter body carrying an angioplasty balloon formed of nondistendable polymer, said catheter body having a length of about 75–150 cm and defining a first and second lumen, said first lumen sized to slideably receive a guidewire for delivery of said catheter over a guidewire through said vessel to the stenosis, and said second lumen extending from the proximal end and including a port open to the interior of the balloon for introducing inflation fluid from the proximal end of said catheter to inflate said balloon, the balloon including a dilatation section, proximal taper section, and a distal taper section, said dilatation section extending substantially parallel to the axis of the catheter when the balloon is in the inflated state and over a sufficient length for engaging and dilating the stenosis by forcing the stenosis open under dilatation pressure, wherein the length of the dilatation section is greater than the combined length of the proximal and distal taper sections, said proximal taper section having a gradual proximal slope to the catheter for providing a gradual, atraumatic profile upon withdrawal of said catheter from the blood vessel after dilatation, and said distal taper section having an abrupt distal slope extending a short length compared to said proximal taper section.

14. The catheter of any one of claims 11–13 wherein said proximal taper section has a transition taper angle of about 3–15° and a distal taper section has a transition taper angle of about 10–35°.

15. The catheter of claim 14 wherein said proximal taper section has a transition taper angle of about 10° and said distal taper section has a transition taper angle of about 20°.

16. The catheter of claim 14 wherein said distal and proximal taper sections have differing transition taper angles selected to maintain a balloon volume that is in the range equal to or less than the volume of a balloon having the same dilatation section length and inflation diameter and proximal and distal taper sections of a matching transition taper angle between 8–12°.

17. The catheter of any one of claims 11–13 wherein said balloon is composed of polymer including polyethyleneterephthalate.

18. The catheter of any one of claims 11–13 wherein the proximal taper section has a transition taper angle of about 3 to 15°.

19. The catheter of any one of claims 11–13 wherein said angioplasty balloon is a multilayer balloon.

20. The catheter of claim 19 wherein said angioplasty balloon includes an inner layer of polyethyleneterephthalate.

21. The catheter of claim 19 wherein said angioplasty balloon includes an outerlayer of elastomer.

* * * * *

UNITED STATES PATENT AND TRADEMARK OFFICE
CERTIFICATE OF CORRECTION

PATENT NO.    : 6,129,737
DATED         : OCTOBER 10, 2000
INVENTOR(S)   : BRUCE HAMILTON ET AL.

It is certified that error appears in the above-identified patent and that said Letters Patent is hereby corrected as shown below:

Column 5, Claim 1, Line 65, Delete "end" and Insert - - and- -

Column 6, Claim 11, Line 67, Delete "taier" and Insert - -taper- -

Column 8, Claim 13, Line 11, Insert - -"a"- - before ", proximal"

Signed and Sealed this

Twenty-second Day of May, 2001

*Attest:*

NICHOLAS P. GODICI

*Attesting Officer*    *Acting Director of the United States Patent and Trademark Office*